United States Patent [19]
Adkins et al.

[11] Patent Number: 6,022,937
[45] Date of Patent: Feb. 8, 2000

[54] POLYETHER POLYOLS BASED ON TRIAZOLE GROUP CONTAINING COMPOUNDS AND A PROCESS FOR THEIR PRODUCTION

[75] Inventors: Rick L. Adkins, New Martinsville; Harold R. Parsons, Wheeling, both of W. Va.

[73] Assignee: Bayer Corporation, Pittsburgh, Pa.

[21] Appl. No.: 09/199,223

[22] Filed: Nov. 24, 1998

[51] Int. Cl.$^7$ .................. C08G 18/50; C07D 249/04; C07D 249/08; C07D 249/12; C07D 249/14

[52] U.S. Cl. ................ 528/23; 252/182.24; 252/182.26; 528/49; 528/78; 528/79; 548/255; 548/257; 548/259; 548/262.2; 548/263.2; 548/263.6; 548/263.8; 548/264.2; 548/264.8; 548/267.8; 548/268.6; 568/583; 568/593; 568/606; 568/607; 568/611

[58] Field of Search .................. 252/182.24, 182.26; 528/73, 78, 79, 49; 548/255, 257, 259, 262.2, 263.2, 263.6, 263.8, 264.2, 264.8, 267.8, 268.6; 568/583, 593, 606, 607, 611

[56] References Cited

U.S. PATENT DOCUMENTS

| | | | |
|---|---|---|---|
| 3,000,963 | 9/1961 | Sporanza | 568/621 |
| 3,299,151 | 1/1967 | Wismer et al. | 568/621 |
| 4,110,268 | 8/1978 | Longley et al. | 521/177 |
| 4,380,502 | 4/1983 | Müller et al. | 252/182 |
| 4,430,490 | 2/1984 | Doerge | 528/77 |
| 4,877,879 | 10/1989 | Gansow | 544/402 |
| 5,064,929 | 11/1991 | Kumpf et al. | 528/172 |
| 5,786,405 | 7/1998 | Schilling et al. | 521/167 |

FOREIGN PATENT DOCUMENTS

| | | |
|---|---|---|
| 57-168917 | 10/1982 | Japan . |
| 57-168918 | 10/1982 | Japan . |

*Primary Examiner*—Rabon Sergent
*Attorney, Agent, or Firm*—Joseph C. Gil; N. Denise Brown

[57] ABSTRACT

This invention relates to novel polyether polyols and to a process for their production. These polyether polyols are prepared by forming a polyhydroxyl group containing component in a first step by the reaction of a triazole-group containing compound with a compound that contains at least one functional group that is capable of reacting with the amine groups of the triazole group containing compound, and reacting the hydroxyl-group containing component with an alkylene oxide to form the polyether polyol of the invention. The present invention also relates to isocyanate-reactive compositions comprising these novel polyether polyols, and to a process for the production of a polyurethane comprising reacting a polyisocyanate with the novel polyether polyols of the present invention.

14 Claims, No Drawings

POLYETHER POLYOLS BASED ON TRIAZOLE GROUP CONTAINING COMPOUNDS AND A PROCESS FOR THEIR PRODUCTION

BACKGROUND OF THE INVENTION

This invention relates to a process for the production of polyether polyols based on triazole-group containing hydroxy materials and the novel polyether polyols produced by this process. The present invention also relates to isocyanate-reactive compositions comprising these polyether polyols, and to a process for the production of a polyurethane comprising reacting a polyol and a polyisocyanate wherein the polyol comprises the polyether polyols of the present invention.

Polyether polyols are known in the art for the preparation of polyurethane foams. The polyether polyols are prepared by reacting a polyhydric alcohol such as sucrose, diethylene glycol, trimethylolpropane, etc., with an alkylene oxide such as, for example, ethylene oxide or propylene oxide, in the presence of an alkaline catalyst such as sodium hydroxide. After reaction, the alkaline catalyst is typically removed by one of various methods. Suitable processes for the production of polyether polyols and removal of catalyst residues as are described in, for example, U.S. Pat. Nos. 3,000,963, 3,299,151, 4,110,268, 4,380,502 and 4,430,490.

It is known that the physical and mechanical characteristics of foamed polyurethanes depend, at least to a certain degree, upon the structure and molecular size of the polyethers which are used to produce them.

Amine-initiated polyether polyols and processes for their production are known and described in, for example, U.S. Pat. Nos. 4,877,879 and 5,786,405, and Japanese Abstracts 57168917A and 57168918. These polyether polyols show promising results in foam-forming systems blown without CFC blowing agents. Such polyether polyols can be formed by reacting an amine such as, for example, toluene diamine, with an alkylene oxide such as, for example, ethylene oxide or propylene oxide. This reaction may also be catalyzed with an alkaline catalyst such as potassium hydroxide. The addition of conventional antioxidants such as, for example, butylated hydroxyl toluene (BHT) to the resultant amine-initiated polyether polyols is preferred to minimize color formation in the polyether polyols and foams produced therefrom.

Substantially linear, thermoplastic aromatic polyethers which contain azo groups in the backbone are also known, as disclosed in U.S. Pat. No. 5,064,929. Unlike the above mentioned polyether polyols, however, these thermoplastic polyethers are not precursors in polyurethane reactions. They are instead finished polymers. In addition, they are not hydroxyl-terminated and thus, are incapable of reacting with polyisocyanates. The presence of the internal azo moiety also results in highly colored polymers which would obviously be unsuitable for applications where low color is desirable.

As is commonly known, the reaction of polyols and isocyanates can lead to discolored foam due to chemical or thermal oxidation. This is minimized by the addition to polyether polyols of common antioxidants such as, for example, butylated hydroxy toluene (BHT). In recent years, however, concerns have arisen about the use of low molecular weight antioxidants in PU formulations; concerns relative to the migration of these antioxidants to the surface of the foam, thereby creating exposure problems. The advantage of the present invention is that the antioxidant is chemically bound to the polyether polyol, thereby eliminating the potential for exposure due to the migration of these antioxidants.

SUMMARY OF THE INVENTION

This invention relates to a process for the production of polyether polyols having functionalities of 1 to 10, number average molecular weights of 160 to 32,000, and OH numbers of 7 to 400, and to the novel polyether polyols produced by this process.

This process comprises (1) reacting (a) a triazole-group containing compound with (b) a compound having a molecular weight of from 44 to 7,000 and containing from 1 to 10 functional groups which are capable of reacting with amine groups, to form a hydroxyl-group containing material; and (2) reacting the hydroxyl-group containing material produced in step (1), with (c) an alkylene oxide to form the resultant polyether polyol.

Suitable triazole-group containing compounds are selected from the group consisting of:

(i) an aromatic triazole corresponding to the general formula:

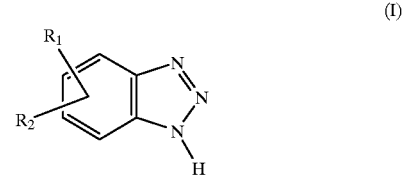

wherein:

$R_1$ and $R_2$: each independently represent a hydrogen atom, an alkyl group containing from 1 to 10 carbon atoms, a hydroxyl group, a carboxyl group, a chlorine atom, a bromine atom or an iodine atom;

(ii) a 1,2,3-triazole group containing compound corresponding to the general formula:

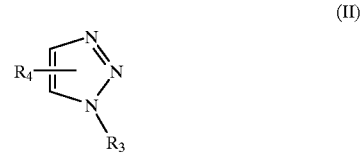

wherein:

$R_3$: represents a hydrogen atom or an amino group; and $R_4$: represents a hydrogen atom, an amino group, or an alkyl group containing from 1 to 10 carbon atoms;

(iii) a 1,2,4-triazole group containing compound corresponding to the general formula:

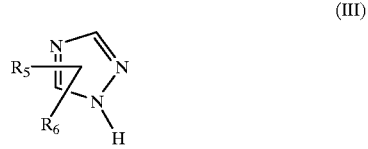

wherein:

$R_5$ and $R_6$: each independently represent a hydrogen atom, an amino group, a thiol group, or an alkyl group containing from 1 to 10 carbon atoms; and (iv) a 1,2,4-triazole-group containing compound corresponding to the general formula:

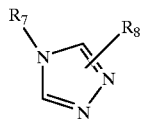

(IV)

wherein:
$R_7$: represents a hydrogen atom or an amino group; and
$R_8$: represents a hydrogen atom, an amino group, a thiol group, or an alkyl group containing from 1 to 10 carbon atoms.

The resultant hydroxyl-group containing materials formed by the reaction of (a) the triazole-group containing compound and (b) the compound having a molecular weight of from 44 to 7,000 and containing from 1 to 10 functional groups which are capable of reacting with amine groups, are characterized by a functionality of from 1 to 10, a molecular weight of from about 160 to 8,000, and an OH number of from 7 to 400.

In accordance with the present invention, there are typically from about 0.8 mole up to about 1.5 moles of triazole-group containing compound, component (a), per mole of compound (b), preferably from about 1 mole up to about 1.2 moles of triazole group containing compound per mole of compound (b). The reaction between components (a) and (b) typically occurs at a temperature of from about 30 to about 150° C., preferably from about 70 to about 110° C.

In the process of preparing the polyether polyols of the present invention, there is typically a minimum of at least about 0.5 moles of alkylene oxide, component (c), per equivalent of hydroxy groups present in the hydroxyl-group containing material formed in step 1). Generally, the pressure for this reaction is from about 15 to about 70 psi and the temperature is from about 80 to about 150° C.

DETAILED DESCRIPTION OF THE INVENTION

Suitable aromatic triazoles for forming the hydroxyl-group containing material of the present invention include those corresponding to the general formula:

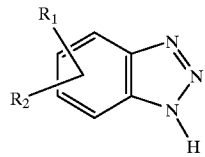

(I)

wherein:
$R_1$ and $R_2$: each independently represent a hydrogen atom, an alkyl group containing from 1 to 10 carbon atoms, a hydroxyl group, a carboxyl group, a chlorine atom, a bromine atom or an iodine atom.

Suitable alkyl groups containing from 1 to 10 carbon atoms may be linear or branched and include groups such as, for example, methyl, ethyl, propyl, butyl, tert-butyl, pentyl, hexyl, ethylhexyl, heptyl, etc.

Some examples of suitable aromatic triazole compounds which correspond to the above formula (I) include compounds such as, for example, tolyltriazole, benzotriazole, chlorobenzotriazole, ethylbenzotriazole, hydroxybenzotriazole, benzotriazole carboxylic acid, etc. Most preferred aromatic triazole compounds are tolyltriazole and benzotriazole.

Suitable 1,2,3-triazole group containing compounds correspond to the general formula:

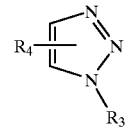

(II)

wherein:
$R_3$: represents a hydrogen atom, or an amino group; and
$R_4$: represents a hydrogen atom, an amino group, or an alkyl group containing from 1 to 10 carbon atoms.

Suitable alkyl groups containing from 1 to 10 carbon atoms may be linear or branched and include groups such as, for example, methyl, ethyl, propyl, butyl, tert-butyl, pentyl, hexyl, ethylhexyl, heptyl, etc.

Some examples of suitable compounds represented by formula (II) above include, but are not limited to 1,2,3-triazole, 4-methyl-1,2,3-triazole, 1-amino-1,2,3-triazole, etc. Most preferred compounds corresponding to formula (II) are 1,2,3-triazole.

Suitable 1,2,4-triazole group containing compounds correspond to the general formula:

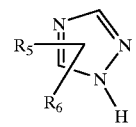

(III)

wherein:
$R_5$ and $R_6$: each independently represents a hydrogen atom, an amino group, a thiol group, or an alkyl group containing from 1 to 10 carbon atoms.

Suitable alkyl groups containing from 1 to 10 carbon atoms may be linear or branched and include groups such as, for example, methyl, ethyl, propyl, butyl, tert-butyl, pentyl, hexyl, ethylhexyl, heptyl, etc.

Suitable examples of compounds corresponding to formula (III) herein above include compounds such as, for example, 1,2,4-triazole, 3-methyl-1,2,4-triazole, 5-methyl-1,2,4-triazole, 3-amino-1,2,4-triazole, 5-amino-1,2,4-triazole, 3,5-diamino-1,2,4-triazole, 3-mercapto-1,2,4-triazole, etc. Most preferred compounds of this group include 3-amino-1,2,4-triazole, 5-amino-1,2,4-triazole and 3,5-diamino-1,2,4-triazole.

Suitable 1,2,4-triazole group containing compounds correspond to the general formula:

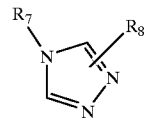

(IV)

wherein:
$R_7$: represents a hydrogen atom or an amino group; and
$R_8$: represents a hydrogen atom, an amino group, a thiol group, or an alkyl group containing from 1 to 10 carbon atoms.

Suitable alkyl groups containing from 1 to 10 carbon atoms may be linear or branched and include groups such as, for example, methyl, ethyl, propyl, butyl, tert-butyl, pentyl, hexyl, ethylhexyl, heptyl, etc.

Some examples of suitable 1,2,4-triazole group containing compounds corresponding to formula (IV) include compounds such as 4-H-1,2,4-triazole, 4-amino-1,2,4-triazole, 3-methyl-4-amino-1,2,4-triazole, etc. A most preferred compound of this group is 4-amino-1,2,4-triazole.

Suitable compounds to be used as component (b) of the present invention include those compounds having a molecular weight of from 44 to 7,000 and containing from 1 to 10 functional groups which are capable of reacting with amine groups, to form a hydroxyl-group containing material. The resultant hydroxyl-group containing material produced by this reaction is characterized by a functionality of from 1 to 10, a molecular weight of from about 160 to 8,000, and an OH number of from 7 to 400.

Suitable compounds to be reacted with the above described triazole-group containing compounds include, for example, those compounds having molecular weights of from about 44 to about 7,000, and containing from 1 to 10 functional groups that are capable of reacting with amine groups from the triazoles. Suitable functional groups for these compounds include, for example, epoxide groups, halide groups, such as, for example, chloride, bromide, fluoride, iodide, etc.

In accordance with the present invention, when (a) the triazole compound contains only secondary amine groups, and component (b) contains only one functional group capable of reacting with the amine groups of the triazoles, this functional group is not a halide group unless one or more hydroxyl groups are also present in this component.

Some examples of suitable compounds for component (b) include those compounds which contain one group capable of reacting with an amine group of the triazole-group containing compounds. Component (b) compounds containing one amine-reactive group include compounds such as, for example, ethylene oxide, propylene oxide, butylene oxide, styrene oxide, tetrahydrofuran, etc., 2-haloethanols, such as, for example, 2-chloroethanol, 2-fluoroethanol, 2-bromoethanol, etc., glycidol, 3-halo-1,2-propanediols, such as, for example, 3-chloro-1,2-propanediol, 3-fluoro-1, 2-propanediol, etc.

Suitable compounds for use as component (b) of the present invention also include difunctional materials which contain two functional groups capable of reacting with amine groups of the triazole-group containing compound. Some examples of such difunctional materials include compounds such as, for example, epichlorohydrin, 1,3-butadiene diepoxide, bisphenol A diglycidyl ether, 2,2-bis (bromomethyl)-1,3-propanediol, 2,2-bis(chloromethyl)-1,3-propanediol, etc., 3-[bis-(glycidyloxymethyl)methoxy]-1,2-propanediol, 1,2,7,8-diepoxy-octane, ethylene glycol diglydicyl ether, etc.

Suitable compounds containing three or more amine-reactive groups include, for example, epoxidized polyisoprene, epoxidized linseed oil, trimethylolpropane, triglycidyl ether, pentaerythritol tetraglycidyl ether, etc.

Suitable alkylene oxides for reacting with the hydroxyl-group containing compounds produced in step (1) of the present invention include those alkylene oxides typically used in forming conventional polyether polyols. Some examples of such alkylene oxides include compounds such as ethylene oxide, propylene oxide, butylene oxide, styrene oxide, tetrahydrofuran, etc. Preferred alkylene oxides for the present invention include compounds such as ethylene oxide and propylene oxide.

It is possible, at least in theory, that the compound used as component (b) could be the same as the compound used as component (c) in the present invention. It is preferred, however, that different compounds are used as component (b) and as component (c).

In general, the reaction between the triazole-group containing compound and the compound having a molecular weight of from about 44 to about 7,000 and which contains from 1 to 10 functional groups that are capable of reacting with amine groups of the triazole-group containing compound is typically by adding the compound containing the amine-reactive groups to the triazole-group containing compound at a temperature of 150° C. or less. The reaction with, for example, an epoxide is exothermic, while the reaction with, for example, a chloride is less so and it requires some heat. Solvent can be used in the reaction, but is not essential. The reaction is completed once the triazole-group containing compound is consumed. The resultant hydroxyl-group containing material formed in step (1) is used as is (i.e., unpurified) to form a polyether polyol by reaction with an alkylene oxide.

Polyether polyols in accordance with the present invention can be prepared by any of the known processes such as are described in, for example, U.S. Pat. Nos. 4,209,609 and 4,421,871, the disclosures of which are herein incorporated by reference, and as described in British Patent 1,398,185. In general, the polyether polyols of the present invention are prepared by reacting an alkylene oxide with a hydroxyl-group containing compound (as formed in step (1) above) having a functionality of at least 1, optionally in the presence of an alkaline catalyst.

Some examples of alkylene oxides useful in producing the polyether polyols of the present invention include: ethylene oxide, propylene oxide, butylene oxide, and mixtures of these alkylene oxides. Combinations of ethylene oxide and propylene oxide are particularly preferred. In principle, any alkaline material capable of catalyzing the epoxidation reaction of the present invention may be used. Specific alkaline catalysts which have been found to be particularly suitable include compounds such as, for example, but are not limited to, potassium hydroxide and sodium hydroxide.

In general, the epoxidation reaction occurs by contacting the hydroxyl-group containing compound formed in step (1) of the process that is characterized by a functionality of at least 1 with the alkylene oxide(s) at an elevated temperature in the range of from 90 to 180° C. under moderately elevated pressure, optionally in the presence of the alkaline catalyst. The epoxidation product generally has an average hydroxyl value (determined by ASTM D-2849-69 hydroxyl number method C) of at least 7, preferably in the range of from about 100 to about 400. The molecular weights of the polyether polyols of the present invention (number average determined by end group analysis and nominal functionality of the polyol) generally range from about 160 to about 32,000, preferably from about 300 to about 1200, most preferably from about 400 to about 1000.

If an alkaline catalyst is used in the preparation of the polyether polyol, the resultant reaction mixture which contains the alkaline catalyst in amounts of from about 0.1% to about 1.0% as KOH is neutralized with an acid such as, for example, sulfuric acid, phosphoric acid, lactic acid or oxalic acid. Neutralization may be accomplished by mixing the acid and reaction mixture at ambient conditions with stirring, then distilling to remove any excess water. The neutralized polyether polyol need not have a pH of exactly 7.0. The reaction mixture may be maintained at a slight acidity or alkalinity, i.e., at a pH of from 5 to 11, preferably from 6 to 10. If the salt formed is soluble in the polyol, it may be left in. Otherwise, the salt can be removed by, for example, filtration.

The neutralized polyether polyol reaction mixture of the present invention is clear, i.e., free from haze and may be used directly in processes for the production of polyurethane foams. A suitable process for the production of polyurethanes by reacting the novel triazole based polyether polyols of the present invention with polyisocyanates via the polyisocyanate addition process. Suitable polyisocyanates for such a process include, for example, aliphatic, cycloaliphatic, araliphatic, and aromatic polyisocyanates.

This invention also relates to isocyanate-reactive compositions comprising the polyether polyols of the present invention.

The following examples further illustrate details for the process of preparation and use of the compositions of this invention. The invention, which is set forth in the foregoing disclosure, is not to be limited either in spirit or scope by these examples. Those skilled in the art will readily understand that known variations of the conditions and processes of the following preparative procedures can be used to prepare these compositions. Unless otherwise noted, all temperatures are degrees Celsius and all parts and percentages are parts by weight and percentages by weight, respectively.

EXAMPLES

Example 1

Tolyltriazole (826 g) was heated to 100° C. in a flask until completely melted. Glycidol (506 g) was slowly added, while maintaining the temperature at approximately 100° C. using an ice water bath. The reaction was held at this temperature for about two hours, then cooled to obtain the desired hydroxyl-group containing product, which was a tan liquid. This intermediate hydroxyl-group containing product was analyzed by mass spectrometry to confirm the structure as follows:

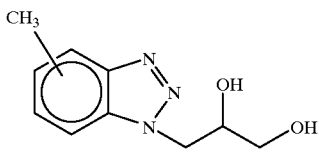

The tan liquid hydroxyl-group containing material (1320 g) prepared above was reacted with propylene oxide (5919 g) in the presence of KOH catalyst at 110° C. The liquid product was neutralized with sulfuric acid and the solids were filtered off. The resultant liquid product was characterized by an OH number of 128 and a viscosity of 344 cps.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a polyether monool or polyether polyol having a functionality of 1 to 10, a number average molecular weight of 160 to 32,000, and an OH number of 7 to 400, comprising:
   (1) reacting
      (a) a triazole-group containing compound selected from the group consisting of:
         (i) an aromatic triazole corresponding to the general formula:

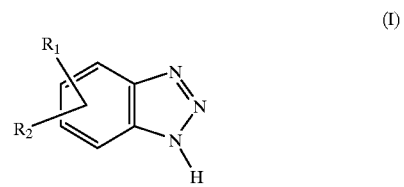

wherein:
   $R_1$ and $R_2$: each independently represent a hydrogen atom, an alkyl group containing from 1 to 10 carbon atoms, a hydroxyl group, a carboxyl group, a chlorine atom, a bromine atom or an iodine atom;
      (ii) a 1,2,3-triazole group containing compound corresponding to the general formula:

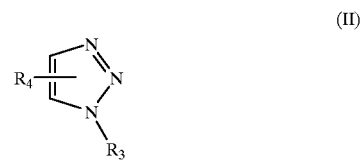

wherein:
   $R_3$: represents a hydrogen atom or an amino group, and
   $R_4$: represents a hydrogen atom, an amino group, or an alkyl group containing from 1 to 10 carbon atoms;
      (iii) a 1,2,4-triazole group containing compound corresponding to the general formula:

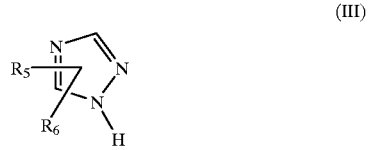

wherein:
   $R_5$ and $R_6$: each independently represent a hydrogen atom, an amino group, a thiol group, or an alkyl group containing from 1 to 10 carbon atoms; and
      (iv) a 1,2,4-triazole-group containing compound corresponding to the general formula:

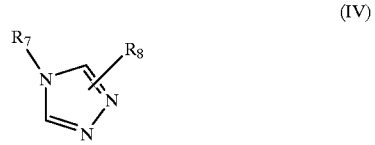

wherein:
   $R_7$: represents a hydrogen atom or an amino group, and
   $R_8$: represents a hydrogen atom, an amino group, a thiol group or an alkyl group containing from 1 to 10 carbon atoms; with
   (b) a compound having a molecular weight of from 44 to 7,000 and containing from 1 to 10 functional groups which are capable of reacting with amine groups,
thereby forming a hydroxyl-group containing material, said hydroxyl-group containing material having a functionality of from 1 to 10, a molecular weight of from about 160 to about 8,000, and an OH number of from about 7 to about 400; and 2) reacting the hydroxyl-group containing material produced in step 1) with (c) an alkylene oxide to form the resultant polyether polyol.

2. The process of claim 1, wherein component (a) the triazole-group containing compound and component (b) the compound having a molecular weight of from 44 to 7,000 and containing from 1 to 10 functional groups which are capable of reacting with amine groups from component (a) are present in amounts such that there are from about 0.8 mole up to about 1.5 moles of component (a) per mole of component (b).

3. The process of claim 2, wherein component (a) and component (b) are present in amounts such that there are from about 1 mole up to about 1.2 moles of component (a) per mole of component (b).

4. The process of claim 1, wherein the reaction between components (a) and (b) occurs at a temperature between about 30 to about 150° C.

5. The process of claim 1, wherein component (c) the alkylene oxide is present in an amount such that there are at least about 0.5 mole of alkylene oxide present per equivalent of hydroxy groups present in the hydroxyl-group containing compound formed in step (1).

6. The process of claim 1, wherein (a)(i) is selected from the group consisting of tolyltriazole, benzotriazole, chlorobenzotriazole, ethylbenzotriazole, hydroxybenzotriazole, benzotriazole carboxylic acid, and mixtures thereof.

7. The process of claim 2, wherein (a)(i) is selected from the group consisting of tolyltriazole and benzotriazole.

8. The process of claim 1, wherein (a) is selected from the group consisting of 1,2,3-triazole, 3-amino-1,2,4-triazole, 5-amino-1,2,4-triazole, 3,5-diamino-1,2,4-triazole, 4-amino-1,2,4-triazole and mixtures thereof.

9. The process of claim 1, wherein component (b) contains one or more functional groups, said functional groups being selected from the group consisting of epoxide groups, halide groups and mixtures thereof.

10. The process of claim 1, wherein the reaction of the hydroxyl-group containing compound formed in step 1) with (c) the alkylene oxide component occurs in the presence of an alkaline catalyst.

11. The process of claim 10, wherein the resultant polyether monool or polyether polyols are neutralized.

12. The polyether monool or polyether polyols produced by the process of claim 1.

13. In a process for the production of a polyurethane, comprising reacting a polyisocyanate with an isocyanate-reactive component, the improvement wherein the isocyanate-reactive component comprises the polyether monool or polyether polyol of claim 12.

14. An isocyanate-reactive composition comprising at least one polyol, wherein the polyol comprises the polyether monool or polyether polyol of claim 12.

* * * * *